(12) United States Patent
Perkins et al.

(10) Patent No.: US 8,090,076 B2
(45) Date of Patent: Jan. 3, 2012

(54) COLLIMATION APPARATUS FOR RADIOTHERAPY

(75) Inventors: Clifford William Perkins, West Sussex (GB); Christopher Charles Knox, West Sussex (GB)

(73) Assignee: Elekta AB (publ), Stockholm (SE)

( * ) Notice: Subject to any disclaimer, the term of this patent is extended or adjusted under 35 U.S.C. 154(b) by 44 days.

(21) Appl. No.: 12/601,387

(22) PCT Filed: May 24, 2007

(86) PCT No.: PCT/EP2007/004625
§ 371 (c)(1),
(2), (4) Date: Nov. 23, 2009

(87) PCT Pub. No.: WO2008/141667
PCT Pub. Date: Nov. 27, 2008

(65) Prior Publication Data
US 2010/0166150 A1 Jul. 1, 2010

(51) Int. Cl.
*G21K 1/02* (2006.01)
(52) U.S. Cl. .................. 378/152; 378/147
(58) Field of Classification Search .......... 378/145–153
See application file for complete search history.

(56) References Cited

U.S. PATENT DOCUMENTS
4,868,844 A * 9/1989 Nunan .......................... 378/152

FOREIGN PATENT DOCUMENTS
| EP | 0259989 A1 | 3/1988 |
|---|---|---|
| EP | 0286858 A | 10/1988 |
| EP | 0314214 A2 | 5/1989 |
| FR | 2524655 A1 | 10/1983 |
| GB | 1029859 A | 5/1966 |
| GB | 2367993 A | 4/2002 |
| GB | 2403884 A | 1/2005 |

OTHER PUBLICATIONS

Lind, B, et al.: "Development of Treatment Techniques for Radiotherapy Optimization", International Journal of Imaging Systems and Technology, Wiley and Sons, New York, US, vol. 6, No. 1, Mar. 1, 1995, pp. 33-42.
International Search Report, Oct. 16, 2007.
PCT Written Opinion of the International Search Authority, PCT/EP2007/004625 (2007).

* cited by examiner

Primary Examiner — Hoon Song
(74) Attorney, Agent, or Firm — Westman, Champlin & Kelly, P.A.; Z. Peter Sawicki

(57) ABSTRACT

A radiotherapy apparatus comprises a means for producing a beam of radiation directed along a beam axis and having a width in first and second directions transverse to the beam axis, a multi-leaf collimator for selectively limiting the width of the beam in at least the first direction, a block collimator for selectively limiting the width of the beam in at least the second direction, the block collimator comprising a diaphragm moveable into and out of the beam and having a thickness in the direction of the beam axis that varies. The diaphragm can have a front edge of greater thickness than at least one region behind the front edge. It can also have a spine region extending from a rear part thereof towards the front edge that is greater thickness than at least one region displaced laterally with respect thereto. Together, these can cover the areas that will not be fully shadowed by a dynamically moving MLC.

19 Claims, 6 Drawing Sheets

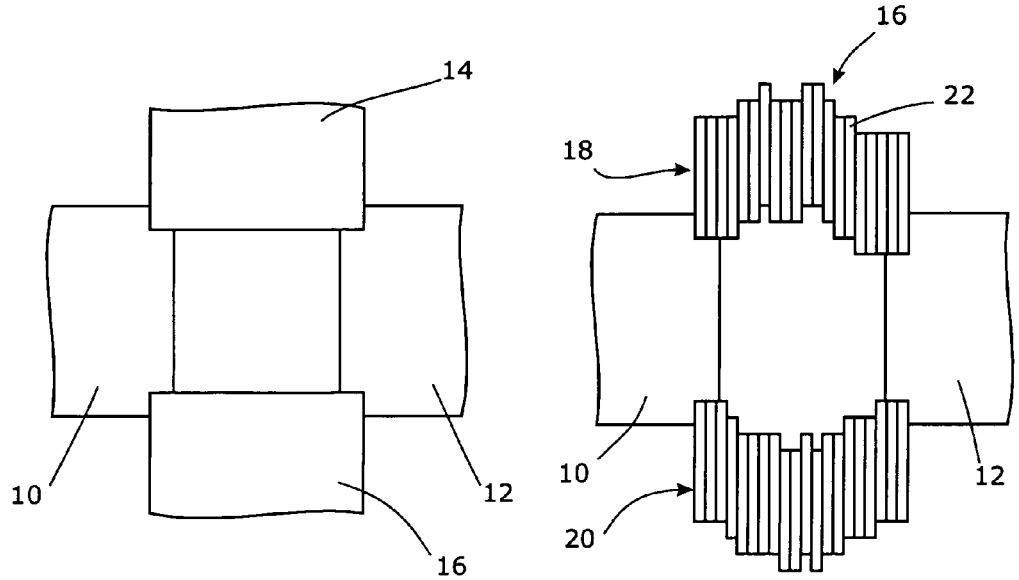
Fig 1
PRIOR ART
Fig 2
PRIOR ART
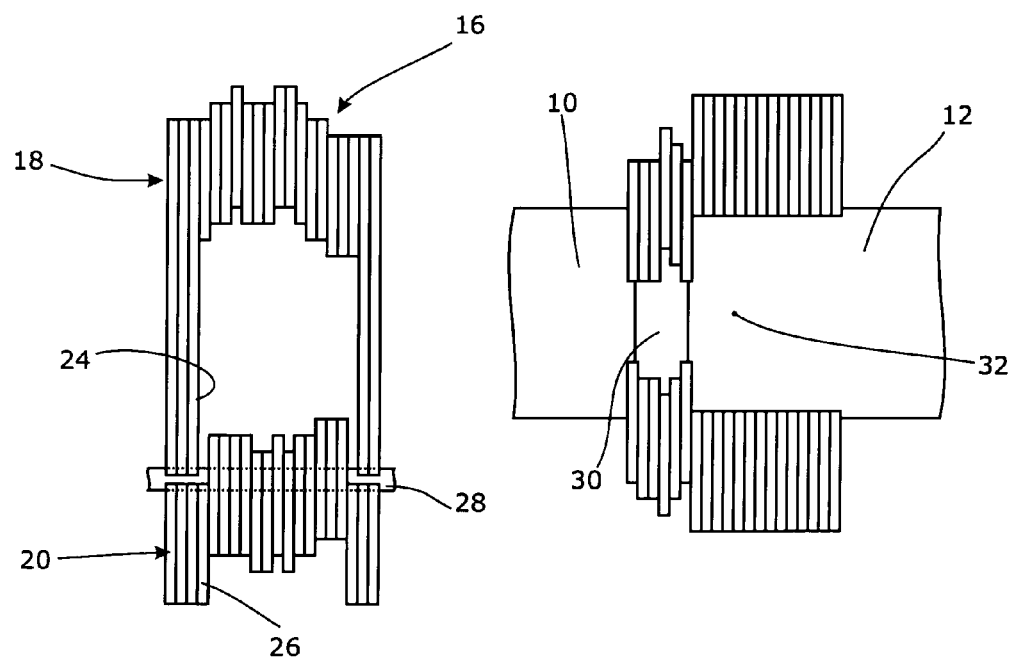
Fig 3
PRIOR ART
Fig 4

US 8,090,076 B2

COLLIMATION APPARATUS FOR RADIOTHERAPY

This Application is a Section 371 National Stage Application of International Application No. PCT/EP2007/004625, filed May 24, 2007 and published as WO 2008/141667 A1 on Nov. 27, 2008, the content of which is hereby incorporated by reference in its entirety.

FIELD OF THE INVENTION

The present invention relates to collimation apparatus for radiotherapy.

BACKGROUND ART

The technique of radiotherapy involves directing a beam of harmful high-energy radiation towards a tumour. The radiation causes damage to the tumour cells which, over time, destroys the cancer. As the beam is harmful, it is necessary to limit the radiation dose that is applied to the healthy tissue, whilst at the same time maintaining the dose delivered to the tumour. Accordingly, some means needs to be provided to de-limit the radiation beam so that its size is no larger than is necessary or achievable. Early radiotherapy machines used a collimation system as shown schematically (along the beam's eye view) in FIG. 1, in which two sets of moving shielding blocks (known as diaphragms) move in mutually perpendicular directions x and y, both axes being perpendicular to the radiation beam (z). Thus, a first pair of blocks 10, 12 move in an x direction to the limit the transverse width of the beam (as viewed in FIG. 1). A second pair of blocks 14, 16 move in the y direction so as to de-limit the width of the beam in that axis. In this way, a beam of any chosen rectangular size up to a maximum achievable size could be used.

Tumours are not generally rectangular, however. As a result, it is now common to use a so-called "multi leaf collimator", which is made up of individual thin "leaves" of a high atomic number material such as tungsten, each of which can move independently in and out of the beam path in order to block the beam. FIG. 2 shows a generalised multi-leaf collimator which replaces the y collimators 14, 16 of FIG. 1. The x collimators 10 and 12 remain. Thus, the multi-leaf collimator 16 consists of a first bank 18 and a second bank 20, each comprising a large number of thin leaves 22, narrow in the x direction transverse to the beam and relatively long in the y direction transverse to the beam and the z direction parallel to the beam. Their length in the z direction allows sufficient opacity to the x-ray or other beam to achieve an effective shielding effect, and their length in the y direction allows them to be extended into and out of the beam in that direction so as to define any chosen shape.

In some cases, as shown in FIG. 3, the remaining pair of diaphragms 10, 12 are dispensed with altogether, and the leaves are made sufficiently long to shut off the beam completely by overlapping or passing right across the beam as shown in the case of (for example) leaf 24. The join between opposing leaves 24, 26 can either be placed underneath an offset blocking strip 28 (as shown in FIG. 3) or can be achieved by placing the leaves at different points along the z axis so that the two leaves 24, 26 can overlap when viewed in the z direction. This arrangement does, however, mean that the width of the beam in the x direction can only be one of an integer number times the width of the leaves. The arrangement shown in FIG. 2 allows any dimension of a beam width since the x collimators 10, 12 can be moved as desired.

Prior to the development of the MLC, beams were delimited to the shape of the tumour insofar as existing collimation arrangements permitted. When the multi-leaf collimator became available, novel forms of treatment were made possible such as conformal arc radiotherapy, in which the shape of the beam conforms at all times to the projected shape of the tumour along the instantaneous axis of the beam. This minimises radiation dose to healthy tissue either side of the tumour, and in combination with a rotating source that is able to direct a beam towards the patient from a range of different directions, can result in a very high dose within the tumour and a very small dose outside the tumour.

Conformal arc therapy can, however, only deliver a convex-shaped dose, i.e. one in which the dose steadily decreases away from the dose centre. Further developments in the use of multi-leaf collimators have included techniques such as intensity modulated radiotherapy (IMRT) and other techniques in which more complex shapes created by the multi-leaf collimator allow non-convex dose distributions to be built up over time. Generally, the MLC does not irradiate the entire tumour continuously in such techniques, and otherwise difficult but useful dose shapes can be developed such as a cylindrical dose conforming to the shape of a patient's hip in which (for example) a bone tumour is irradiated leaving the sensitive organs within the hip largely unirradiated. These can result in a need for an off-centre radiation field, as shown schematically in FIG. 4; the radiation field 30 is displaced from the beam's central axis 32, and in order to do this one x collimator 12 is extended across the beam beyond the central axis 32.

SUMMARY OF THE INVENTION

Assuming that the beam aperture is 40 cm at the collimators, beam shapes such as those shown in FIG. 2 require the x collimators 10, 12 to traverse from a fully withdrawn (or "20 cm open") position to a 0 cm position at which they extend to the central axis of the beam. In order to provide beam shapes such as that shown in FIG. 4, a further 15 cm or so of extension also is required. This will not translate into a complete blocking of the beam by one diaphragm only, but generally this is not clinically required. A 15 cm offset beyond the beam's central axis will suffice for most clinically useful shapes.

It should be remembered however that in order to shield the full beam, the diaphragms are required to be of the order of 8 cm thick solid tungsten material. That additional 15 cm of 8 cm thick tungsten imposes a significant weight burden on the diaphragms. Correspondingly, the mechanism required to move a significantly greater mass of diaphragm will be correspondingly heavier itself. Both of these increase the overall mass of the treatment head, which in turn causes the apparatus structure to deflect more, resulting in a less accurate treatment. It should be borne in mind that most clinical accelerators place the treatment head at the end of a long arm which is mounted on a rotatable support so that the treatment head can be rotated around the patient. Additional mass at the end of that arm causes the arm to deform in a direction which will vary (relative to the treatment head) as the treatment head traverses in an arc around the patient. The present invention therefore seeks to provide a diaphragm which is able to offer the necessary blocking of the radiation beam over a large proportion of the aperture (if necessary), whilst having minimal mass.

The present invention therefore provides a radiotherapy apparatus comprising a means for producing a beam of radiation directed along a beam axis and having a width in first and second directions transverse to the beam axis, a multi-leaf collimator for selectively limiting the width of the beam in at least the first direction, a block collimator for selectively limiting the width of the beam in at least the second direction, the block collimator comprising a diaphragm moveable into and out of the beam and having a thickness in the direction of the beam axis that varies.

The diaphragm can have a front edge of greater thickness than at least one region behind the front edge. It can also have a spine region extending from a rear part thereof towards the front edge that is greater thickness than at least one region displaced laterally with respect thereto. Together, these can cover the areas that will not be fully shadowed by a dynamically moving MLC.

A control means for the multi-leaf collimator can be arranged to extend leaves of the multi-leaf collimator to shadow regions of the beam that are blocked by a relatively thinner section of the diaphragm. This is made easier if the spine region extends from the rearmost part of the diaphragm, the spine region extends to the front edge of the diaphragm, the spine region is straight, the spine region is a central region of the diaphragm, and if the width of the spine region increases towards the front edge of the diaphragm.

Generally, the first and second directions will be mutually transverse.

The present invention also relates to a radiotherapy apparatus comprising a multi-leaf collimator and a block collimator, the block collimator comprising a diaphragm with variable thickness.

In a further aspect, the present invention provides a block collimator for use in radiotherapy apparatus comprising a diaphragm moveable into and out of a beam, and having a thickness in the direction of the beam axis that varies.

In a still further aspect, the present invention provides a radiotherapy apparatus comprising a means for producing a beam of radiation directed along a beam axis and having a width in first and second directions transverse to the beam axis, a multi-leaf collimator for selectively limiting the width of the beam in at least the first direction, a block collimator for selectively limiting the width of the beam in at least the second direction, the block collimator comprising a diaphragm moveable into and out of the beam and having a width that varies transverse to the direction of movement. Thus, parts of the diaphragm can be essentially reduced to zero thickness, leaving a central spine region and a wider front edge that preferably extends across substantially the entire width of the beam in the first direction.

BRIEF DESCRIPTION OF THE DRAWINGS

An embodiment of the present invention will now be described by way of example, with reference to the accompanying figures in which;

FIG. 1 shows a beam's-eye view of a known block collimation arrangement;

FIG. 2 shows a beam's-eye view of a known multi-leaf collimator and block collimator arrangement;

FIG. 3 shows a beam's eye view of a known multi-leaf collimator arrangement;

FIG. 4 shows the desired collimation effect to be achieved by the present invention;

DETAILED DESCRIPTION OF THE EMBODIMENTS

Figure 5:
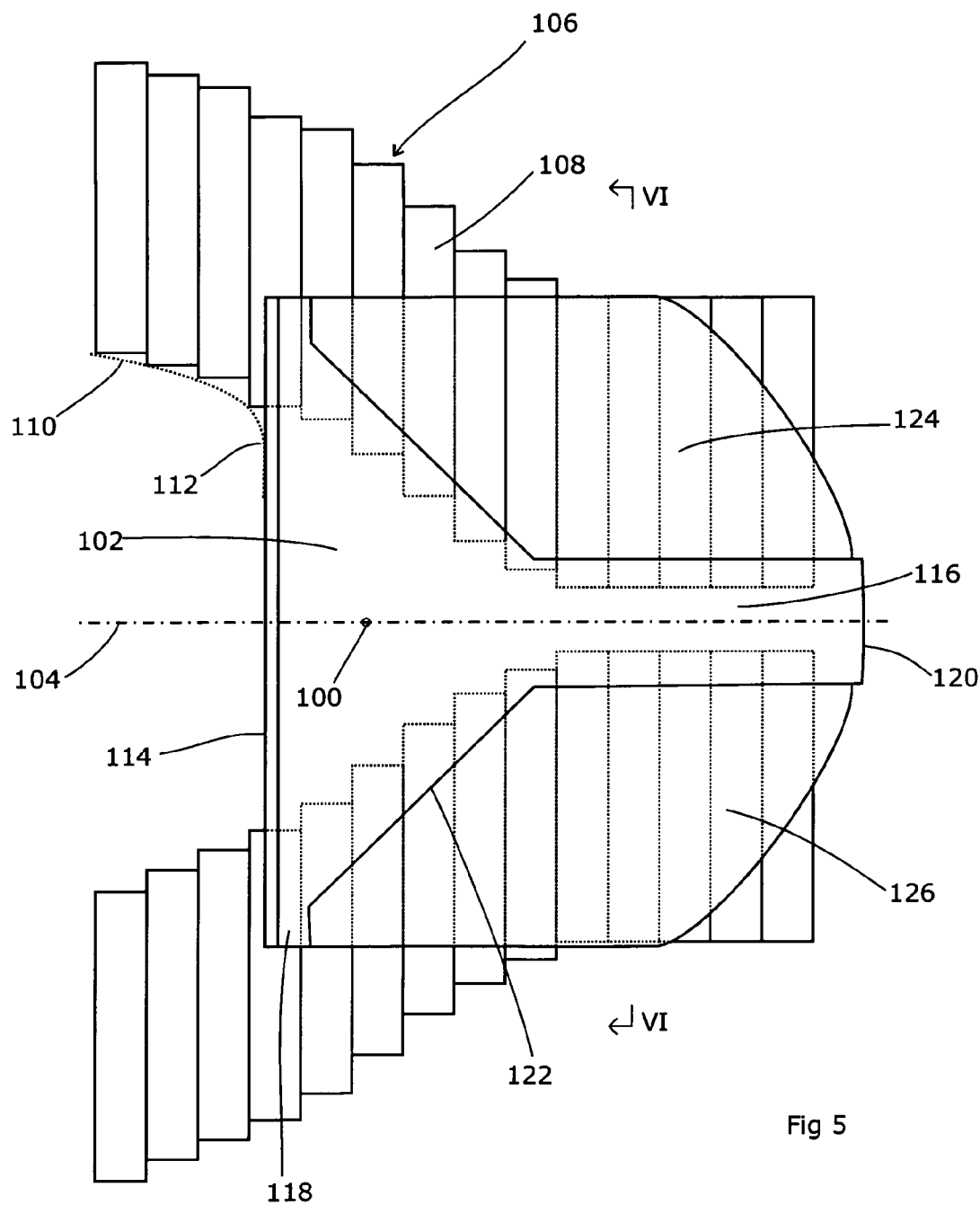
FIG. 5 shows a beam's-eye view of the multi-leaf collimator and block collimator arrangement according to the present invention.

Referring to FIG. 5, showing the view along the beam axis 100, a diaphragm 102 is moveable in and out along an X axis 104 so as to selectively shield the beam to a desired degree. Only the right-hand diaphragm 102 is shown in FIG. 5; there will be a corresponding left-hand diaphragm on the other side which, in this embodiment, is of like construction although it need not be.

A multi-leaf collimator 106 operates in the Y axis. The multi-leaf collimator 106 (MLC) comprises a number of individual leaves 108 which can be extended into and out of the beam along a y axis perpendicular to the diaphragm axis 104. Each leaf can be selectively moved by a desired distance so as to shape the beam to a chosen curved outline such as that shown at 110. The extremity 112 of the curve 110 in the x axis is then met by the diaphragm 102. This both covers the inevitable small degree of leakage between the leaves 108, and allows for the possibility that the extremity 112 does not coincide with a leaf edge. Normally, leaves 108 that are behind the front edge 114 of the diaphragm 102 are redundant and can be withdrawn (as shown in FIG. 4).

The diaphragm 102 of FIG. 5 comprises a central spine region 116 and a front edge 118. The spine region 116 is shown as being centrally located on the diaphragm 102. This is an arrangement which is straightforward and offers a balanced diaphragm, but which is not essential. Both the spine 116 and the front edge 118 are of a relatively increased thickness, to the full thickness normally associated with a diaphragm for a block collimator. Typically, this is of the order of 8 cm thick. The central spine region 116 extends from a rearmost edge 120 of the diaphragm along its central axis 104 until it reaches the front edge 118 of the diaphragm. Approximately half way along the length of the diaphragm, the spine region 116 begins to widen at 122, becoming steadily wider until it is approximately 80-90 percent of the width of the diaphragm at the point where it meets the thicker front edge 118. This thickened "Y"-shaped region of the diaphragm 102 is bounded on either side by generally thinner regions 124, 126. These generally thinner regions are only a fraction of the thickness of the spine and front edge, typically 1-3 cm and preferably about 2 cm. Whilst this is not thick enough to block the therapeutic beam entirely, it is thick enough to cover leakage between MLC leaves adequately. Accordingly, under the control of a suitable control means integrated within the radiotherapy apparatus, the leaves 108 of the MLC are advanced so as to cover the regions 124, 126 of the diaphragm that are of lesser thickness and (as shown) overlap slightly with the spine region 116. Accordingly, an adequate shadow is cast in the beam over all of the areas to be collimated out.

The widening portion 122 of the spine 116 allows for the MLC leaves 108 to "catch up" as the diaphragm 102 moves forward. Generally, leaves 108 will be withdrawn to a greater extent in front of the diaphragm 102, and therefore as the diaphragm 102 moves forward to extend beyond a complete leaf, then that leaf will have a reasonable traverse distance in order to reach the central axis 104 of the block collimator. This traverse will take some time, and therefore the relatively greater width of the spine in 116 in the region 122 allows for this, as can be seen in FIG. 5.

Meanwhile, the thinner portions 124, 126 are of greatly reduced weight, thereby reducing the weight of the diaphragm to an acceptable level yet still permitting extension of the diaphragm significantly beyond the central axis 100 of the beam.

Figure 6:
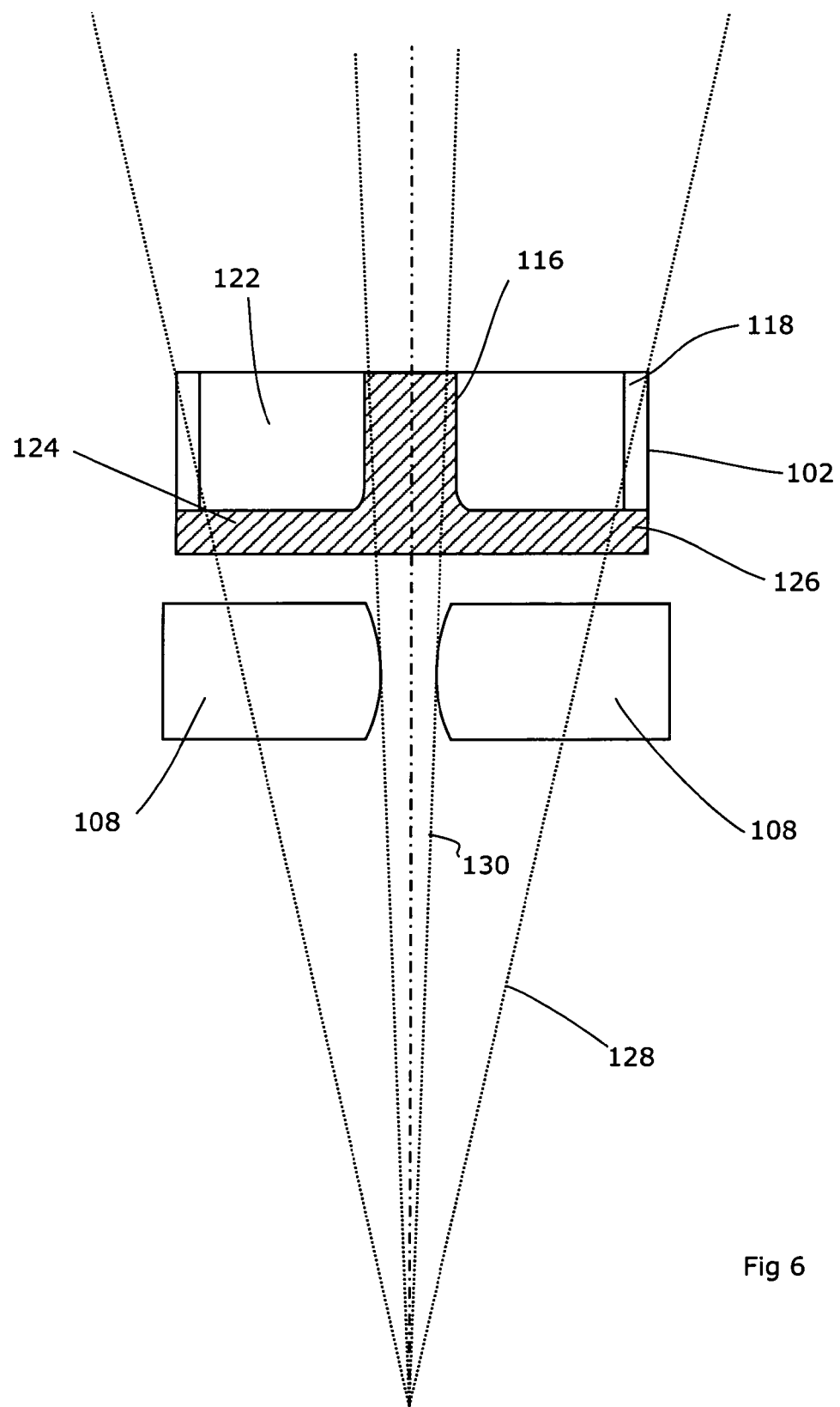
FIG. 6 shows a section along the beam axis showing the beam, leaves of the multi-leaf collimator, and a section through the block collimator.

FIG. 6 shows a section along the beam axis along the lines VI-VI on FIG. 5. The leaves 108 of the multi-leaf collimator extend so as to collimate the beam 128 down to a narrower section 130 which corresponds (in this embodiment) to the minimum approach distance of the opposing leaves. Leaves are not permitted to move more closely, in order to prevent them from touching and being damaged. This narrow section 130 is then entirely within the spine section 116 of the block collimator 102. The thinner regions 124, 126 are entirely within the shadow of the MLC leaves 108.

Figure 7:
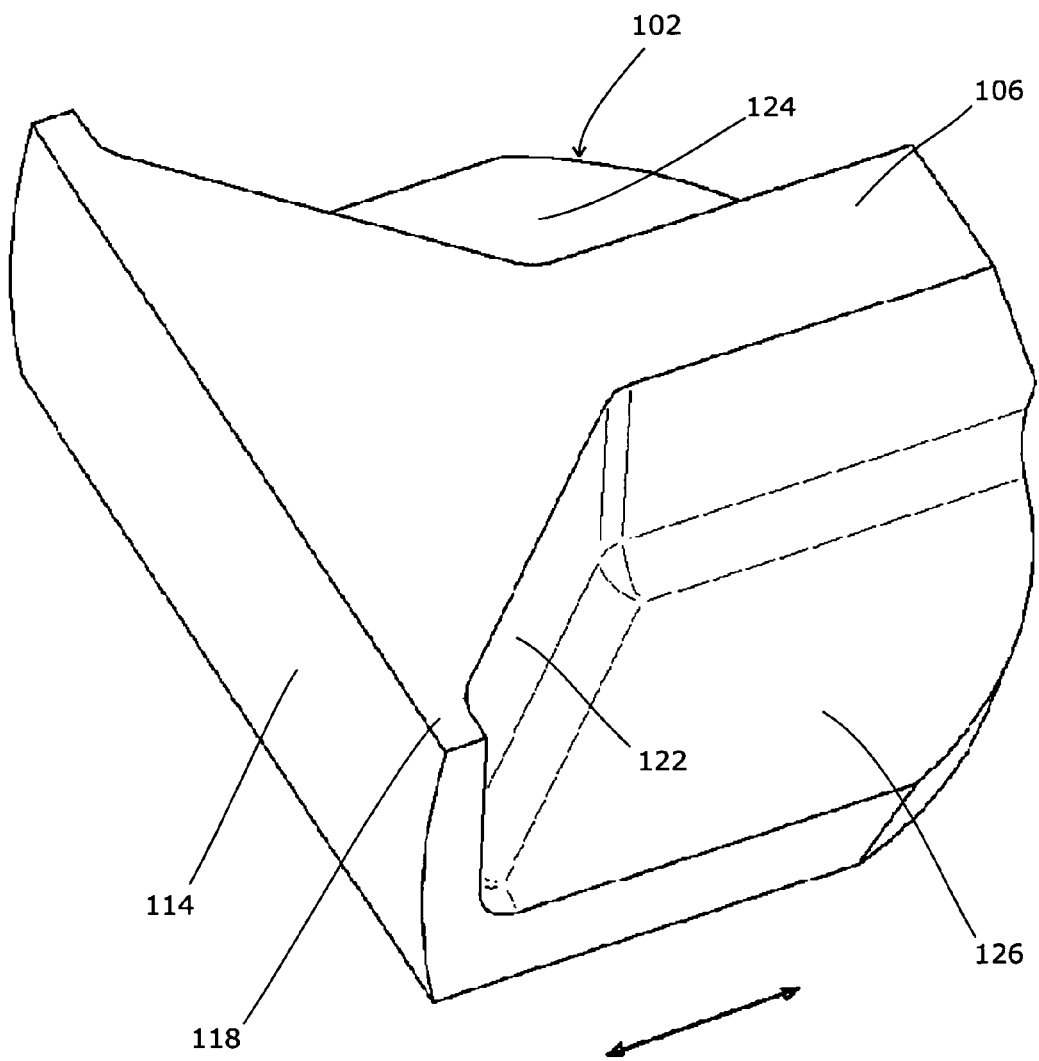
FIG. 7 shows a perspective view of the diaphragm of the block collimator.

FIG. 7 shows the diaphragm 102 in a perspective view. A curved front edge 114 allows for a minimum penumbra regardless of the position of the diaphragm 102 (and hence the incident angle of the radiation) in a generally known manner. Other arrangements are however possible that employ a flat front face; either the penumbra is accepted, or the diaphragm follows an arcuate path so that the front face remains aligned with the beam direction. The thickened front edge 118 extends across the full width of the diaphragm 102, and the spine region 106 extends in a straight line from the rear of the diaphragm 102 to the front edge 114 along the central axis of the diaphragm 102. Approximately half way along the diaphragm 102, it widens in the region 122 in a linear manner so that by the point where the spine 106 reaches the thickened front edge 118, it is approximately 80-90 percent of the width of the diaphragm. Thinner regions 124, 126 either side of the central spine region 106 allow for considerable weight reduction.

Figure 8:
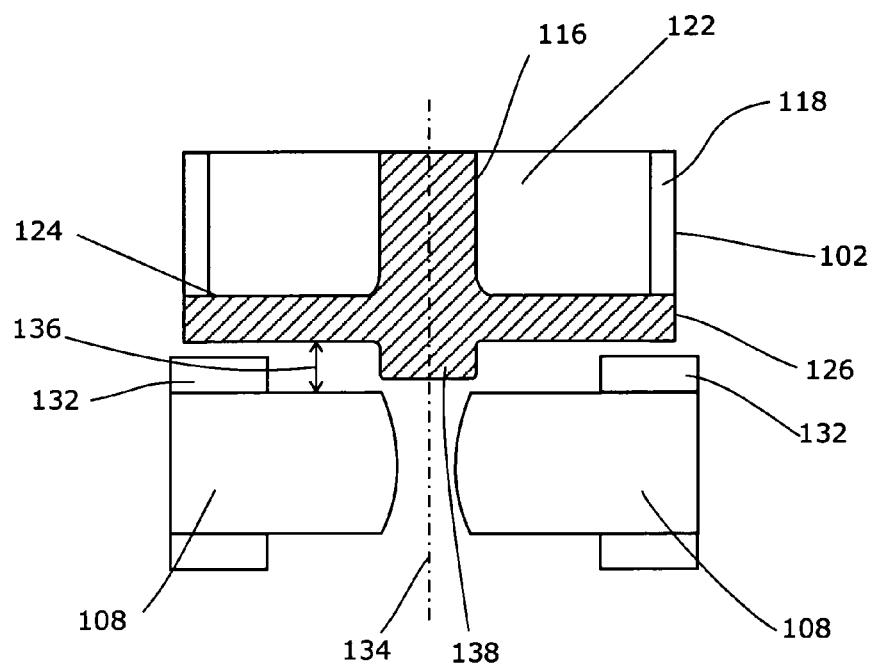
FIG. 8 shows a section of an alternative embodiment along the beam axis.

FIG. 8 shows an alternative design. This relies on the fact that many MLC systems support the leaves 108 in a carriage 132, which extends above and below the leaves and supports the upper and lower edges thereof. The carriage 132 does not itself extend to the centre of the beam, although it may move into and out of the beam field in order to carry the leaves forward and permit a greater extension of the leaves into and/or across the field. The carriage does however have a defined thickness in the beam direction 134, which means that there is a corresponding spacing 136 between the upper edge of the leaves 108 and the lower face of the diaphragm 102.

As the carriages 132 do not extend to the centre of the field, however, this spacing 136 is unnecessary in the region beneath the spine 116 if the latter is centrally located. If the spine 116 is not central with respect to the diaphragm, then the availability of space will depend on where the spine is located relative to the position or range of movement of the carriages 132. Accordingly, in this embodiment the spine 116 also projects below the lower face of the diaphragm at 138. This means that more material can be placed in the spine region, improving the opacity of the diaphragm system. Alternatively, a corresponding amount of material can be removed from the upper edge of the spine, thereby reducing the overall depth of the collimator system and hence the radiation head, and improving the flexibility of the apparatus as a whole.

Figure 9:
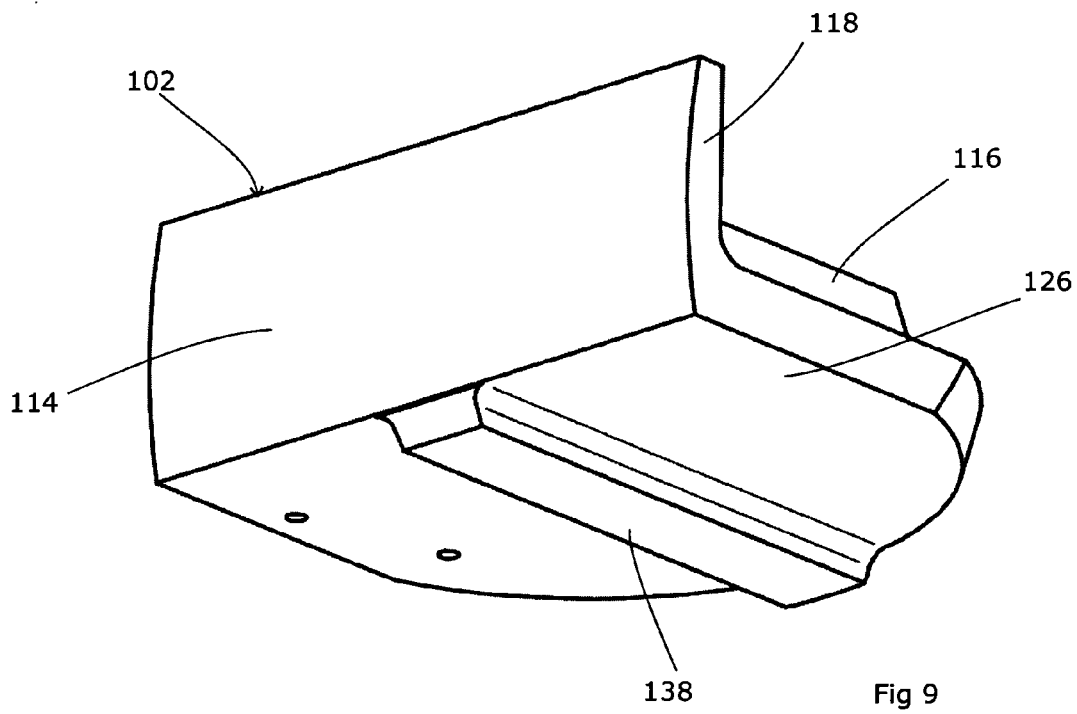
FIG. 9 shows the diaphragm of FIG. 8 in perspective from below.

FIG. 9 shows a perspective view from beneath of the diaphragm of FIG. 8. The lower projection 138 of the spine 116 can clearly be seen, extending rearwardly from the curved front face 114 of the diaphragm to the rear edge beneath the spine 116. The lower projection could also include an additional section partly or fully corresponding to the widening region 122, depending on the location and any range of movement of the MLC carriages 132.

Figure 10:
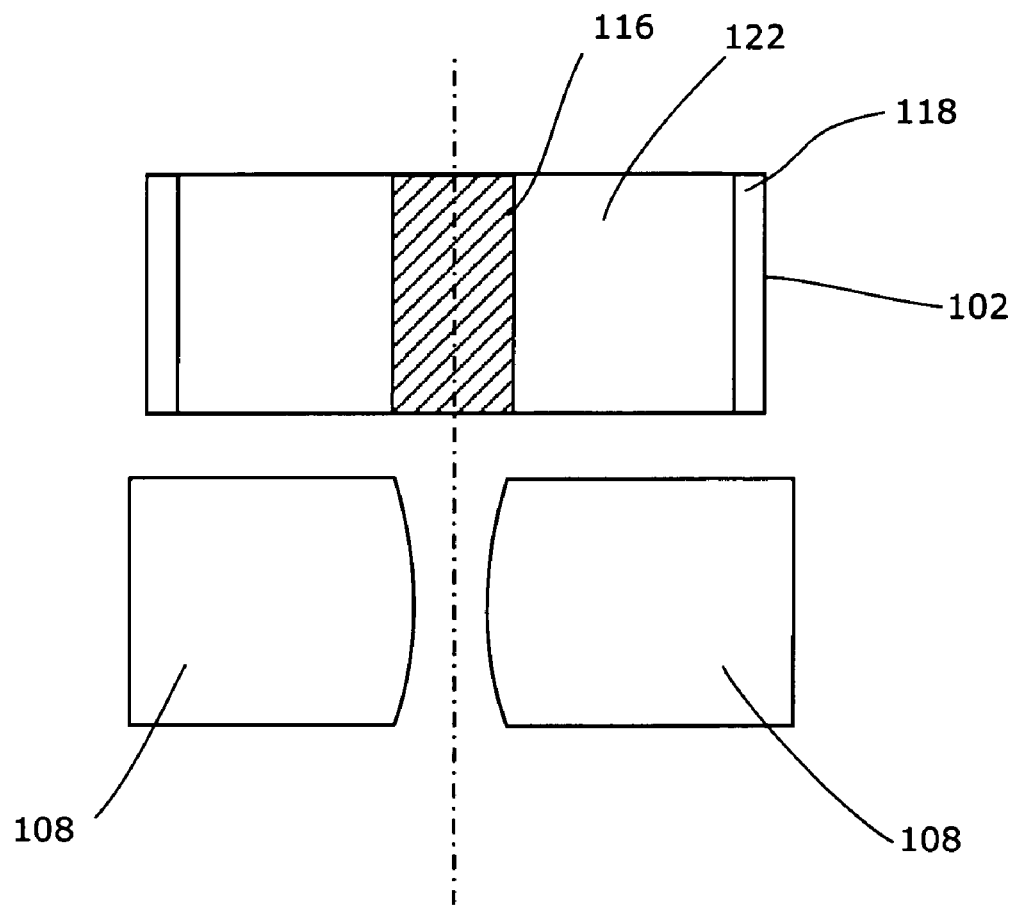
FIG. 10 shows a section of a further alternative embodiment along the beam axis.

FIG. 10 shows a further embodiment. The purpose of the thinner regions 124, 126 either side of the spine 116 is to provide a back-up shield behind the extended MLC leaves 108. This caters for concerns that there may be some transmission through the MLC leaves, for example between leaves. Efforts are however made to eliminate such sources of leakage, and it may be that such backup is considered unnecessary. In that case, further weight saving can be achieved by eliminating the thinner regions completely and adopting a design as shown in FIG. 10. The diaphragm 102 consists simply of a front edge 118 and a spine 116, with the widening portion 122 between thereby defining a Y-profile when viewed along the beam axis.

If the speed of movement of the MLC leaves is felt to be sufficient, or if the intended speed of the diaphragm is low enough, the widening portion 122 can be omitted leaving, potentially, a simple T-profile diaphragm.

Only a single spine is shown in the accompanying figures. However, it is possible to envisage a diaphragm having a plurality of spines, which would offer a choice of locations as to where to park opposing leaves. This additional flexibility may be useful in clinical situations, although it will reduce slightly the weight savings obtainable through the present invention.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A radiotherapy apparatus comprising;
  a means for producing a beam of radiation that is directed along a beam axis and has a width in first and second directions transverse to the beam axis;
  a multi-leaf collimator for selectively limiting the width of the beam in at least the first direction;
  a block collimator for selectively limiting the width of the beam in at least the second direction;
  wherein the block collimator comprising a diaphragm moveable into and out of the beam and having a thickness that varies in the direction of the beam axis and in which the diaphragm has a spine region extending from a rear part thereof towards the front edge that is of greater thickness than at least one region displaced laterally with respect thereto.

2. The radiotherapy apparatus according to claim 1 in which the diaphragm has a front edge of greater thickness than at least one region behind the front edge.

3. The radiotherapy apparatus according to claim 1 in which the spine region extends from the rearmost part of the diaphragm.

4. The radiotherapy apparatus according to claim 1 in which the spine region extends to the front edge of the diaphragm.

5. The radiotherapy apparatus according to claim 1 in which the spine region is straight.

6. The radiotherapy apparatus according to claim 1 in which the spine region is a central region of the diaphragm.

7. The radiotherapy apparatus according to claim 1 in which the width of the spine region increases towards the front edge of the diaphragm.

8. The radiotherapy apparatus according to claim 1 in which the first and second directions are mutually transverse.

9. A radiotherapy apparatus comprising a multi-leaf collimator and a block collimator, the block collimator comprising a diaphragm with variable thickness and a spine region in which the spine region has a greater thickness than at least one region displaced laterally with respect thereto.

10. The radiotherapy apparatus according to claim 9, further comprising a control means for the multi-leaf collimator, arranged to extend leaves of the multi-leaf collimator to shadow regions of the beam that are blocked by a relatively thinner section of the diaphragm.

11. A block collimator for use in radiotherapy apparatus comprising a diaphragm moveable into and out of a beam, and having a thickness in the direction of the beam axis that varies and in which the diaphragm has a spine region extending from a rear part thereof towards the front edge that is greater thickness than at least one region displaced laterally with respect thereto.

12. The block collimator according to claim 11 in which the diaphragm has a front edge of greater thickness than at least one region behind the front edge.

13. The block collimator according to claim 11 in which the spine region extends from the rearmost part of the diaphragm.

14. The block collimator according to claim 11 in which the spine region extends to the front edge of the diaphragm.

15. The block collimator according to claim 11 in which the spine region is straight.

16. The block collimator according to claim 11 in which the spine region is a central region of the diaphragm.

17. The block collimator according to claim 11 in which the width of the spine region increases towards the front edge of the diaphragm.

18. A radiotherapy apparatus comprising;
a means for producing a beam of radiation directed along a beam axis and having a width in first and second directions transverse to the beam axis;
a multi-leaf collimator for selectively limiting the width of the beam in at least the first direction;
a block collimator for selectively limiting the width of the beam in at least the second direction;
the block collimator comprising a diaphragm moveable into and out of the beam and having a width that varies transverse to the direction of movement and comprising a central spine region and a wider front edge.

19. The radiotherapy apparatus according to claim 18 in which the wider front edge extends across substantially the entire width of the beam in the first direction.

* * * * *